United States Patent [19]

Reneau

[11] Patent Number: 4,837,390

[45] Date of Patent: Jun. 6, 1989

[54] HYPERBARIC ORGAN PRESERVATION APPARATUS AND METHOD FOR PRESERVING LIVING ORGANS

[75] Inventor: Raymond P. Reneau, Houston, Tex.

[73] Assignee: Keyes Offshore, Inc., Sugarland, Tex.

[21] Appl. No.: 493,600

[22] Filed: May 11, 1983

[51] Int. Cl.[4] .......................... A01N 1/02; C12M 1/00

[52] U.S. Cl. ........................................ 435/1; 435/283; 435/287

[58] Field of Search ........................ 435/1, 3, 283, 289, 435/290, 311, 313, 287; 128/1 R; 422/40, 295

[56] References Cited

U.S. PATENT DOCUMENTS

| | | | |
|---|---|---|---|
| 3,406,531 | 10/1968 | Swenson et al. | 435/283 X |
| 3,545,221 | 12/1970 | Swenson et al. | 435/283 X |
| 3,654,085 | 4/1972 | Norr et al. | 435/283 |
| 3,772,153 | 11/1973 | De Roissart | 435/283 |
| 3,827,251 | 8/1974 | Koski et al. | 128/1 R X |
| 3,843,455 | 10/1974 | Bier | 435/283 |
| 3,881,990 | 5/1975 | Burton et al. | 435/283 X |
| 3,892,628 | 7/1975 | Thorne et al. | 435/283 X |
| 3,914,954 | 10/1975 | Doerig | 435/283 X |
| 3,995,444 | 12/1976 | Clark et al. | 435/283 X |
| 4,186,565 | 2/1980 | Toledo-Pèreyra | 435/1 |

OTHER PUBLICATIONS

Perry, Chemical Engineers' Handbook, New York, McGraw Hill, 1973, pp. 6-56 to 6-57.

*Primary Examiner*—Robert J. Warden
*Assistant Examiner*—Randall E. Deck
*Attorney, Agent, or Firm*—Vinson & Elkins

[57] ABSTRACT

An apparatus (A) and method for preserving living organs extracorporeally in vessel (V) having a hyperbaric chamber (C) therein. The organ (O) stored in chamber (C) is provided with perfusate (P) from a reservoir (R) which is open to the atmosphere and freely accessible for the user who may thereby change or add constituents to the perfusate (P) without depressurizing the apparatus (A).

7 Claims, 1 Drawing Sheet

42
46
O
44
50
38
40
36
34
38
P
C
V
16
14
FM
62
FM
64
P
27
26
32
30
S
28
29
39
R
10
36
20
12
18
22
24

HYPERBARIC ORGAN PRESERVATION APPARATUS AND METHOD FOR PRESERVING LIVING ORGANS

FIELD OF THE INVENTION

This invention relates to apparatus and methods for the preservation of living organs extracorporeally such as is required pending transplantation of organs from one being to another.

BACKGROUND OF THE INVENTION

Organ transplantation and preservation is a field of increasing importance due to the advances in the medical arts and sciences related to organ transplants which have made it possible to transplant a variety of living tissues and organs. It is generally recognized in the art that preservation of living tissue is most effective if the tissue is immersed in a perfusate, nutrient liquid, and is maintained in a refrigerated, hyperbaric environment.

It has been found to be desirable for effective preservation to provide a chamber wherein the temperature is less than 37° C. and the pressure is from two to fifteen bars above ambient atmospheric pressure. Furthermore, it is desirable to perfuse the organ with plasma or other similar fluid which provides the necessary nutrient and oxygen to the organ. This perfusate may also contain additives such as hormones, steroids, penicillin, antibiotics or the like to treat specific conditions found in the organ being preserved. Prior art systems generally provided a hyperbaric chamber for storing the organ under the prescribed environmental conditions and a closed, pressurized reservoir and conduit system as a source of perfusate.

When an organ is being preserved in this manner, the attending physician may require that the perfusate be modified as, for example, to include additives or change the basic composition of the fluid. In the past, the perfusate and the preservation chamber were maintained at equilibrium pressures, either both under hyperbaric conditions or both at ambient pressure. Since it is desirable to provide a hyperbaric environment for the organ, prior preservation systems were closed, pressurized systems, wherein both the perfusate and the preservation chamber were maintained at elevated pressures. In these past systems, it is generally necessary to depressurize the entire system, including the organ preservation chamber, in order to change or modify the perfusate.

It is well known that depressurization of the organ must be done carefully to avoid creating gassy embolisms in the organ tissues. These past systems all suffered from the highly undesirable requirement of having to follow carefully prescribed and time consuming procedures for depressurizing the preservation system each time it was necessary or desired to modify or test the perfusate.

SUMMARY OF THE INVENTION

In contrast to the foregoing, the present invention provides a new hyperbaric organ preservation system and method wherein the perfusate reservoir is maintained at ambient pressure, even though the organ preservation chamber is at the desirable elevated pressure. In the apparatus of the present invention perfusate is maintained in an ambient pressure reservoir which allows the attendant to test, modify, add or delete perfusate without effecting the pressure environment of the organ and thus avoids the need to carefully depressurize the system.

DESCRIPTION OF THE PREFERRED EMBODIMENT

Figure 1:
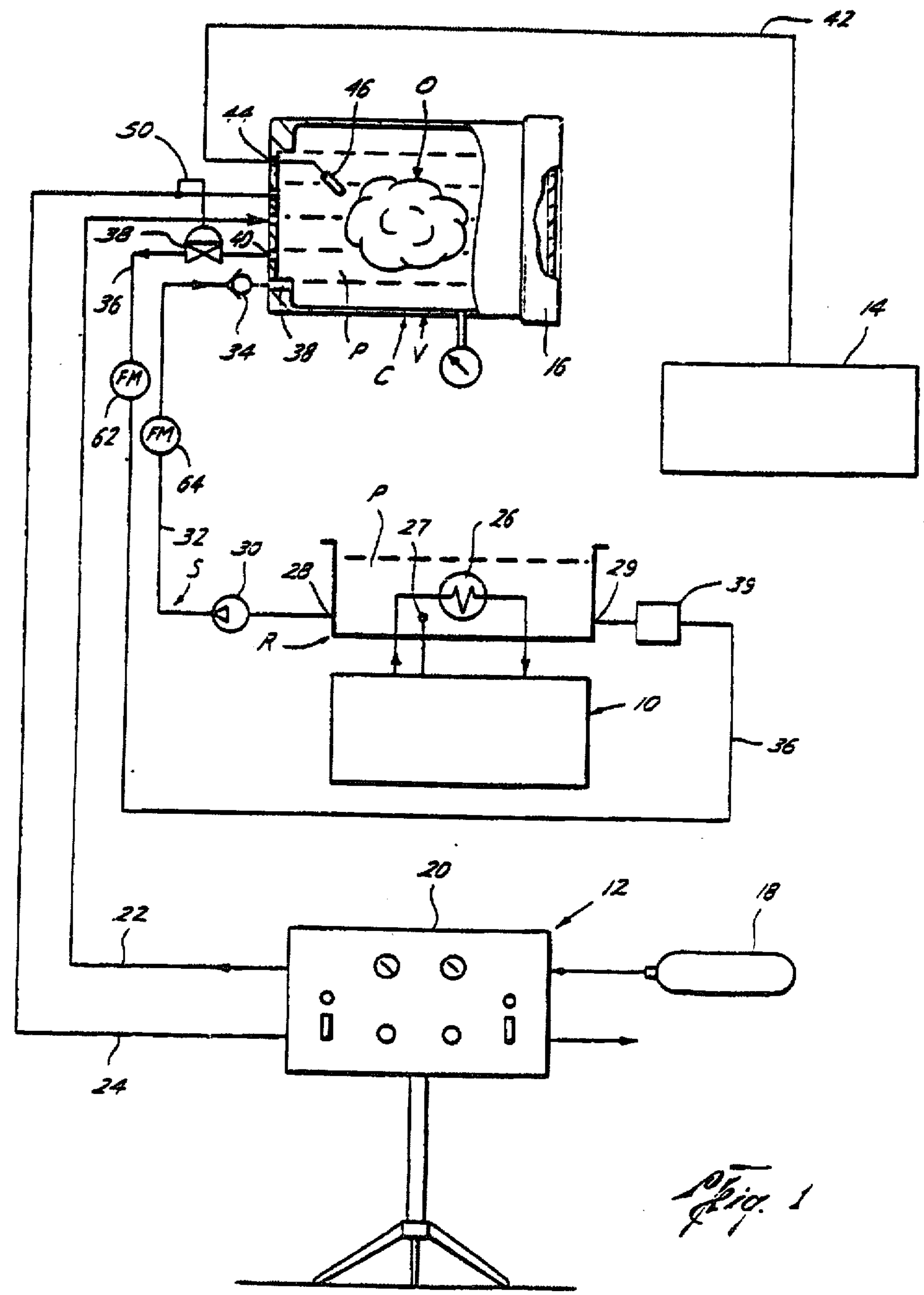
FIG. 1 is a schematic drawing of an organ preservation apparatus of the present invention.

Referring to FIG. 1, the letter A designates generally an organ preserving apparatus according to the present invention. The letter O designates a living organ such as a kidney, liver or a heart which is to be preserved in the apparatus A. Apparatus A includes an organ preservation vessel V formed having a hyperbaric chamber C therein for storing the organ O in a controlled pressurized environment, a perfusate reservoir R, and a perfusate supply system S. The apparatus A is shown in association with peripheral support equipment including a perfusate refrigeration system 10, a regulated high pressure gas supply 12, and an organ condition monitor 14. The various components of apparatus A are shown schematically in FIG. 1 and are not drawn to scale nor with particular structural detail since the structural details of the individual components are matters known to those of ordinary skill in the art. Furthermore, as is also known to those of ordinary skill in the art and hence not specified hereafter, all components of apparatus A which come in direct or indirect contact with the organ O are constructed of suitable biomaterial so that the environment for the organ O will not be contaminated.

The organ O is stored in the hyperbaric chamber C of the organ preservation vessel V and is immersed in a bath of perfusate P. Preferably, chamber C is maintained at a pressure of at least three (3) bars which enhances preservation of the organ O. Perfusate P is life sustaining artificial blood plasma or similar liquid which is circulated from reservoir R to chamber C via perfusate supply system S. The organ preservation vessel V is a high pressure vessel having a sealable door 16 to provide access to the chamber C so that the organ O may be placed therein. The vessel V may be constructed in any suitable conventional manner to provide a pressure tight chamber C capable of withstanding interior pressures up to fifteen (15) bars. While not illustrated, it is also desirable to provide the vessel V with at least one transparent window so that organ O may be observed without opening the chamber C. Regulated gas supply 12 may be any suitable apparatus for providing a regulated source of high pressure gas, such as oxygen, as is known in the art. In the preferred embodiment, supply 12 includes a source of high pressure gas, such as canister 18, a regulator 20, gas supply conduit 22 and gas vent conduit 24. Regulator 20 includes conventional pressure gauges and control mechanisms to enable the operator to set, adjust and monitor the gas pressure in chamber C of the vessel V.

Reservoir R is a fluid receptacle for perfusate P and may be constructed of any suitable material and in the particular shape or configuration as desired. In the preferred embodiment, reservoir R is constructed with material having a low thermal conductivity to facilitate the refrigeration of perfusate P. Perfusate refrigeration unit 10 is a conventional regulated liquid refrigeration apparatus which uses a coolant such as freon circulated through heat exchanger 26 to effect and control the temperature of perfusate P in reservoir R. Refrigeration unit 10 includes a temperature sensing element 27 to sense the temperature of perfusate P and a suitable thermostat (not illustrated) to form a temperature control signal to maintain the temperature of perfusate P within the prescribed range. Refrigeration unit 10 may be any suitable refrigeration system such as are known in the art which is capable of maintaining the temperature of perfusate P in the range of −10° C. to 40° C. at ambient pressure. If desired, the heat exchanger 26 of refrigeration unit 10 could be mounted within chamber C rather than reservoir R, since the object and function of refrigeration unit 10 is to maintain the temperature of the organ O indirectly by cooling the perfusate P. Thus, the temperature sensing element 27 could alternatively be mounted within the chamber C or within/adjacent to the organ O. Reservoir R is provided with a perfusate outlet 28 and a perfusate return inlet 29 suitably located below the normal perfusate level to permit perfusate to circulate from the reservoir R to chamber C within the vessel V ahd back to reservoir R via the perfusate supply system S.

Supply system S includes a pump 30, a delivery conduit 32, a check valve 34, a return conduit 36, and a back pressure regulator 38. Pump 30 provides fluid pressure to circulate perfusate P from reservoir R to chamber C and may be any suitable pump capable of providing sufficient fluid pressure to deliver perfusate to chamber C when chamber C is pressurized from two (2) to fifteen (15) bars above the ambient pressure of the reservoir R. In the preferred embodiment, pump P provides a steady flow of perfusate P to chamber C, but other types of pumps could be used to provide pulsating flow of perfusate if desired. Selection of the particular type of pump 30 to be used is dependent upon the volume of perfusate P that is necessary to circulate via conduit 32, as well as other factors that are known to those of ordinary skill in the art and thus need not be described herein.

Conduit 32, which may be any suitable conduit for transferring perfusate P, is in fluid communication with reservoir R via outlet 28 and with chamber C of the vessel V via check valve 34 and inlet 37. Check valve 34 and inlet 38 allow unidirectional flow of perfusate P from conduit 32 into chamber C in response to fluid pressure provided by pump 30. Check valve 34 prevents perfusate flow from chamber C via inlet 38 and thus isolates hyperbaric chamber C from the ambient pressure reservoir R.

Back pressure regulator 38 is a conventional pressure regulator and relief valve mechanism which senses the pressure in chamber C through conduit 50 which is in communication with the gas vent conduit 24 and opens to maintain a prescribed fluid pressure differential between chamber C and reservoir R. Regulator 38 permits return circulation of effluent perfusate P to reservoir R via outlet 40 in chamber C, return conduit 36 and inlet 29 in reservoir R. If desired, a filter unit or filtration means 39 may be included interposed between return conduit 36 and reservoir R to remove organ by-products and impurities from the effluent perfusate P. The back pressure regulator 38 and return conduit 36 form the perfusate return means of the present invention. Alternatively, the perfusate return means may include fixed or variable in-line orifices (not shown) which may be mounted in flow communication with conduits 32, 36, respectively, for providing back pressure control, eliminating the need for the back pressure regulator 38 and conduit 50 if desired. Filter unit 39 located in conduit 36 is illustrated schematically in FIG. 1, and may be any suitable plasma filter as are commonly available. Filter unit 39 may alternatively be positioned in conduit 32. Furthermore, flow meters 62, 64 are positioned in fluid communication with conduits 36, 32, respectively, for determining the volumetric amount of perfusate (hence the quantity of additives such as vitamins, minerals, antibiotics and all types of metabolic additives) available to organ O.

If desired, apparatus A may also include peripheral instruments for monitoring the condition of the organ. Monitor 14 is a schematic illustration of such conventional instrumentation and includes a multiple element cable 42 for providing the monitor 14 with electrical signals indicative of the condition of organ O. Cable 42 is shown mounted to vessel V via a sealed mounting 44 which permits access to the chamber C without pressure loss. Cable 42 terminates at probe 46 which is a schematic representation of an electrical sensing instrument as is commonly available, and which provide analogue or digital electrical signals indicative of such organ environmental conditions as the organ temperature, transcutaneous gas pressure, and the tissue oxygen partial pressure.

Thus apparatus A provides a controlled hyperbaric environment for oxygen preservation wherein the organ O is bathed in perfusate P provided from an ambient pressure reservoir R. In use, the organ O is placed in the chamber C of vessel V in a bath of perfusate P provided from reservoir R. Chamber C of vessel V is then pressurized to provide a prescribed, hyperbaric environment for the organ O via regulated oxygen supply 12. Regulator 12 maintains the oxygen pressure inside chamber C at the prescribed level. It has been discovered that an oxygen pressure of at least three (3) bars significantly improves preservation. Perfusate P is circulated under pressure from reservoir R to vessel V into the chamber C to provide oxygen, nutrients and treatment to the organ O as is required. The temperature of the organ O is controlled indirectly by controlling the temperature of perfusate P. Other conditions of the organ O may be monitored via monitor 14.

When the attending physician determines that it is necessary or desirable to add to or modify the constituents of the perfusate P, since reservoir R is maintained at ambient pressure, the attendant need not depressurize any part of apparatus A and in particular need not depressurize the chamber C. The apparatus A is thus a significant advance in the art which eliminates the need for time consuming depressurizing procedures and avoids difficulties such as the development of gassy embolisms when a modification of the perfusate P is desired.

The foregoing disclosure and description of the invention are illustrative and explanatory thereof, and various changes in the size, shape and materials, as well as in the details of the illustrated construction may be made without departing from the spirit of the invention.

I claim:

1. A method for preserving living organs extracorporeally utilizing a perfusate, including the steps of:

storing the organ in a chamber formed in a vessel having a hyperbaric atmosphere;

maintaining a supply of the perfusate in a reservoir under ambient pressure; and, supplying the organ in the chamber with perfusate from the reservoir.

2. The method of claim 1, further including the step of:

changing the constituent components of the perfusate in the reservoir without depressurizing the organ within the chamber at hyperbaric atmosphere.

3. The method of claim 1, wherein said supplying includes the steps of:

pumping perfusate at ambient pressure from said reservoir through a conduit in fluid communication with said reservoir and said hyperbaric atmosphere;

maintaining the pressure differential between said reservoir and said hyperbaric atmosphere.

4. The method of claim 3, further including the steps of:

returning effluent perfusate from said hyperbaric chamber to said reservoir.

5. The method of claim 4, further including the steps of:

filtering the effluent perfusate before returning the effluent perfusate to said reservoir.

6. The method of claim 1, further including the step of:

maintaining the temperature of the organ within a temperature range of −10° C. to 40° C.

7. The method of claim 1, wherein said storing includes maintaining a hyperbaric atmosphere in the chamber of at least three bars.

* * * * *